US006241683B1

(12) United States Patent
Macklem et al.

(10) Patent No.: US 6,241,683 B1
(45) Date of Patent: Jun. 5, 2001

(54) PHONOSPIROMETRY FOR NON-INVASIVE MONITORING OF RESPIRATION

(75) Inventors: Peter T. Macklem, Montreal (CA); Cheng-Li Que, Beijing (CN); Suzanne M. Kelly, Montreal (CA); Krzystof Kolmaga, Pointe-Claire (CA); Louis-Gilles Durand, St-Jean-de-Matha (CA)

(73) Assignees: Institut de recherches cliniques de Montréal (IRCM); McGill University, both of Montreal (CA)

( * ) Notice: Subject to any disclaimer, the term of this patent is extended or adjusted under 35 U.S.C. 154(b) by 0 days.

(21) Appl. No.: 09/255,003

(22) Filed: Feb. 22, 1999

(30) Foreign Application Priority Data

Feb. 20, 1998 (CA) .................................................. 2230077

(51) Int. Cl.$^7$ ....................................................... A61B 5/00
(52) U.S. Cl. ......................... 600/529; 600/534; 600/538; 600/586
(58) Field of Search .............................. 600/529, 532–4, 600/538, 586

(56) References Cited

U.S. PATENT DOCUMENTS

| 4,951,678 | * | 8/1990 | Joseph et al. ......................... 600/586 |
| 5,195,528 | * | 3/1993 | Hok ....................................... 600/538 |
| 5,800,361 | * | 9/1998 | Rayburn ................................ 600/532 |
| 5,957,866 | * | 9/1999 | Shapiro et al. ....................... 600/586 |
| 6,030,350 | * | 2/2000 | Jiang et al. .......................... 600/586 |

OTHER PUBLICATIONS

LeBlanc, P.; Macklem, P. T.; Ross, W. R. D. Breath Sounds and Distribution of Pulmonary Ventilation. American Review of Respiratory Disease 102:10–16;1970.

Shykoff, B. E.; Ploysongsang, Y.; Chang, H. K. Airflow and Normal Lung Sounds. American Review of Respiratory Disease 137:872–876;1988.

Graviely, N.; Cugell, D.W. Airflow Effects on Amplitude and Spectral Content of Normal Breath Sounds. J. Appl. Physiol. 80:5–13, 1996.

Ajmani, A.; Mazumdar, J. ; Jarvis, D.—Spectral Analysis of an Acoustic Respiratory Signal with a View to Developing an Apnea Monitor Australian Physical & Engineering Sciences in Medicine 19:46–52;1996.

Makarenkov, A. P. ; Rudnitskij, A. G.—Diagnosis of Lung Pathologies by Two–Channel Processing of Breath Sounds Akusticheskii Zurnal 41:272–277;1994.

Pasterkamp.H.; Kraman, S. S. ; Wodicka, G. R. Respiratory sounds. Advances Beyond the Stethoscope. American Journal of Respiratory and Critical Care Medicine 156:974–987; 1997.

(List continued on next page.)

*Primary Examiner*—Robert L. Nasser
(74) *Attorney, Agent, or Firm*—Swabey Ogilvy Renault; James Anglehart

(57) ABSTRACT

To compensate for the poor signal-to-noise ratio when transforming a patient tracheal sound signal into a respiration flow signal, the transformed signal is used when the sound signal is above a threshold, and interpolated values are used when the sound signal is below the threshold. A volume of breath signal is reliably obtained. Respiration start/stop is detected either by analyzing the sound signal or by physical measurement of the patient. A wearable device incorporating the sound signal processing method can provide an immediate indication or alarm when the volume of breath signal indicates a condition requiring medical attention.

20 Claims, 15 Drawing Sheets

OTHER PUBLICATIONS

Soufflet, G.; Charbonneau, G.; Polit, M.; Attal, P.; Denjean, A.; Escourrou, P.; Gaultier, C.—Interaction Between Tracheal Sound and Flow Rate: a Comparison of Some Different Flow Evaluations From Lung Sounds IEEE Transactions on Biomedical Engineering, vol. 37, No. 4, Apr. 1990.

Rabiner, L.R.; Gold, B.; and McGonegal, C.A.—An Approach to the Approximation Problem for Non–recursive Digital Filters, IEEE Trans. Audio Electroacoustics, 18(2):83–106, 1970.

* cited by examiner

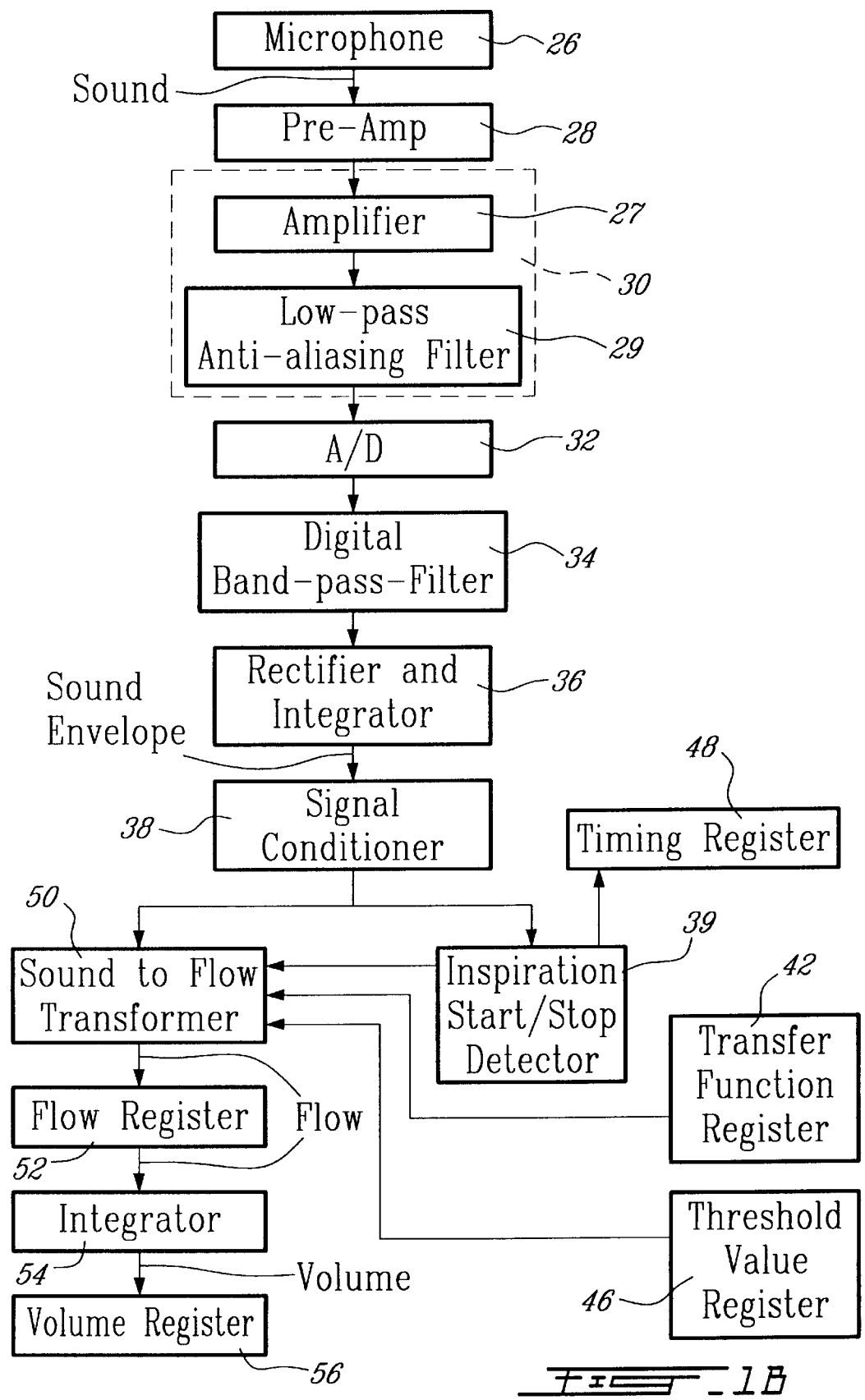

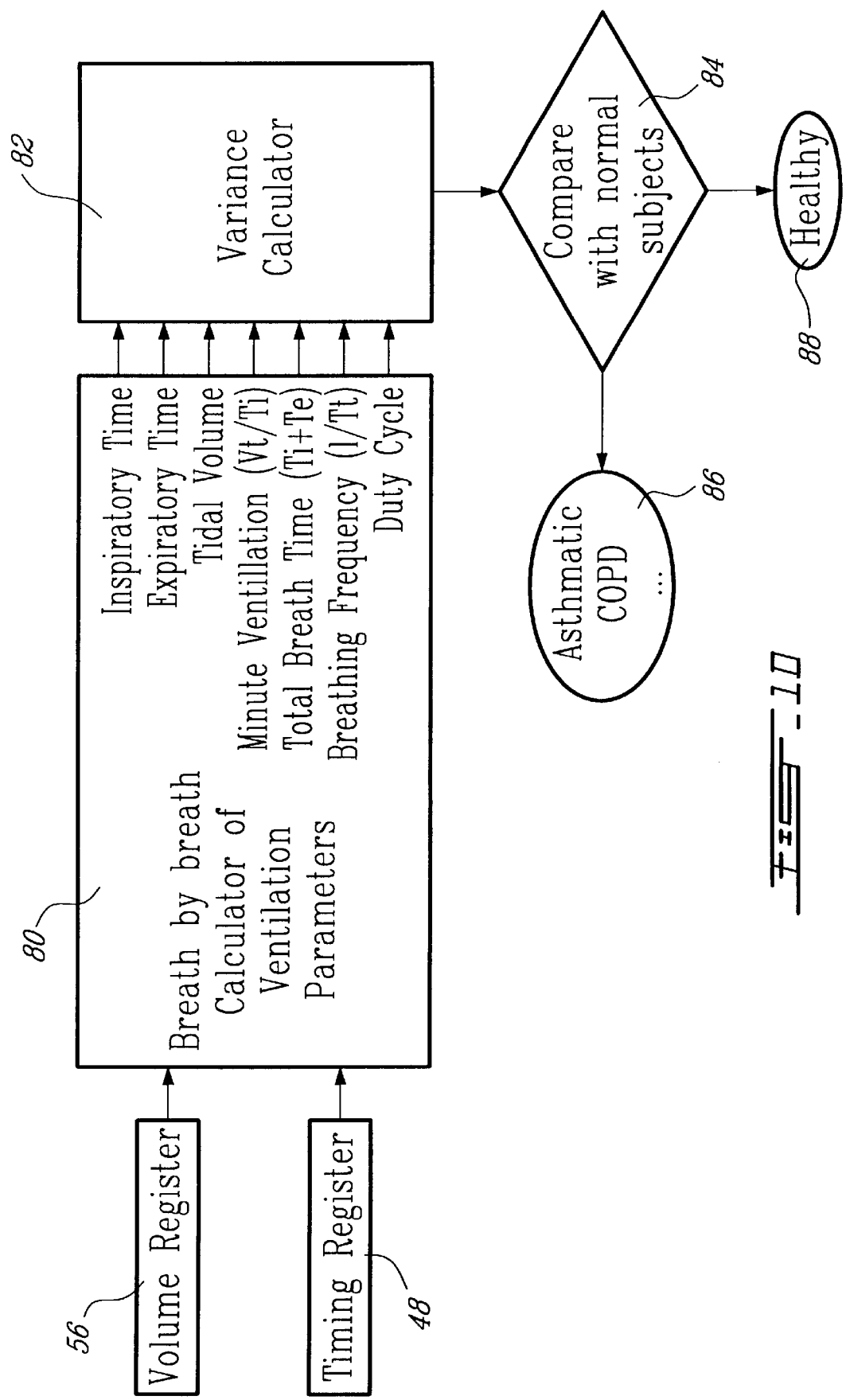

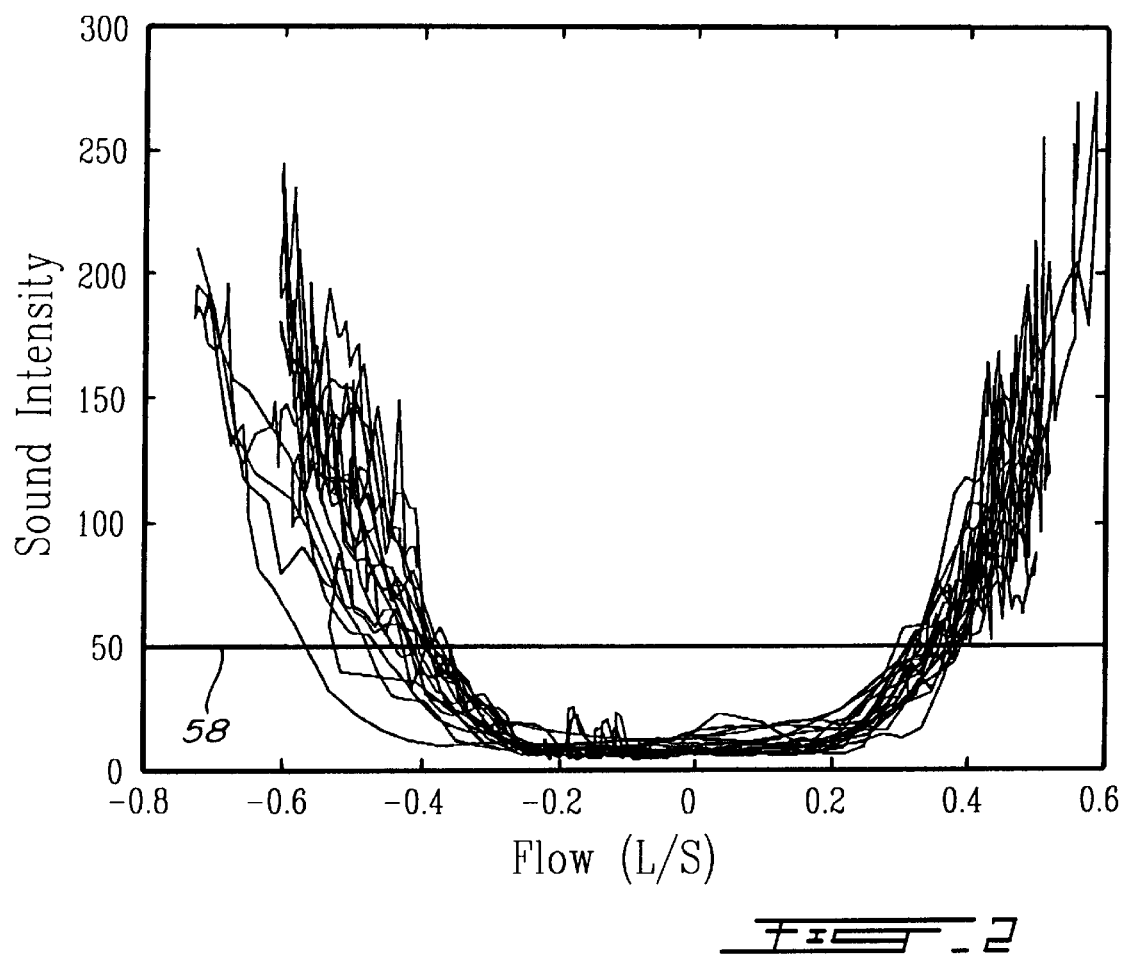

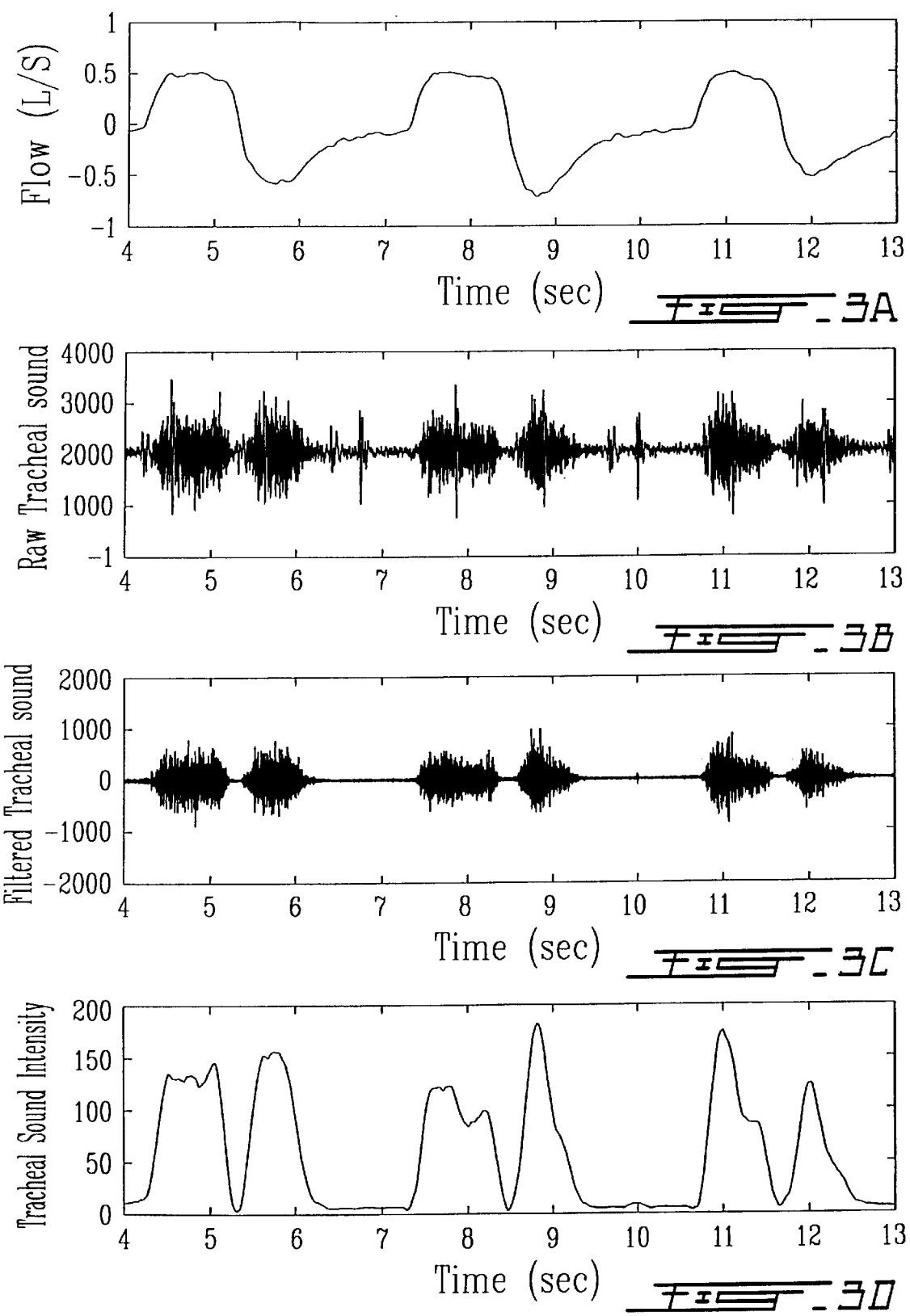

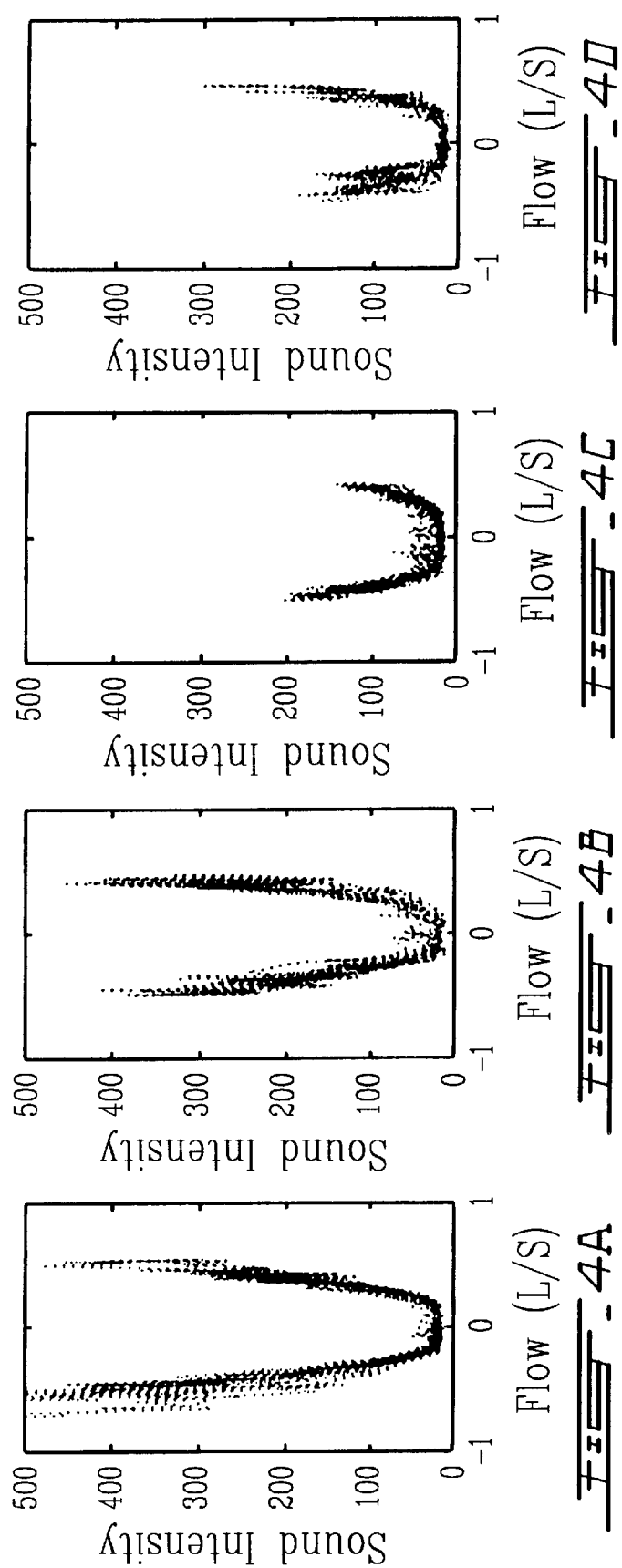

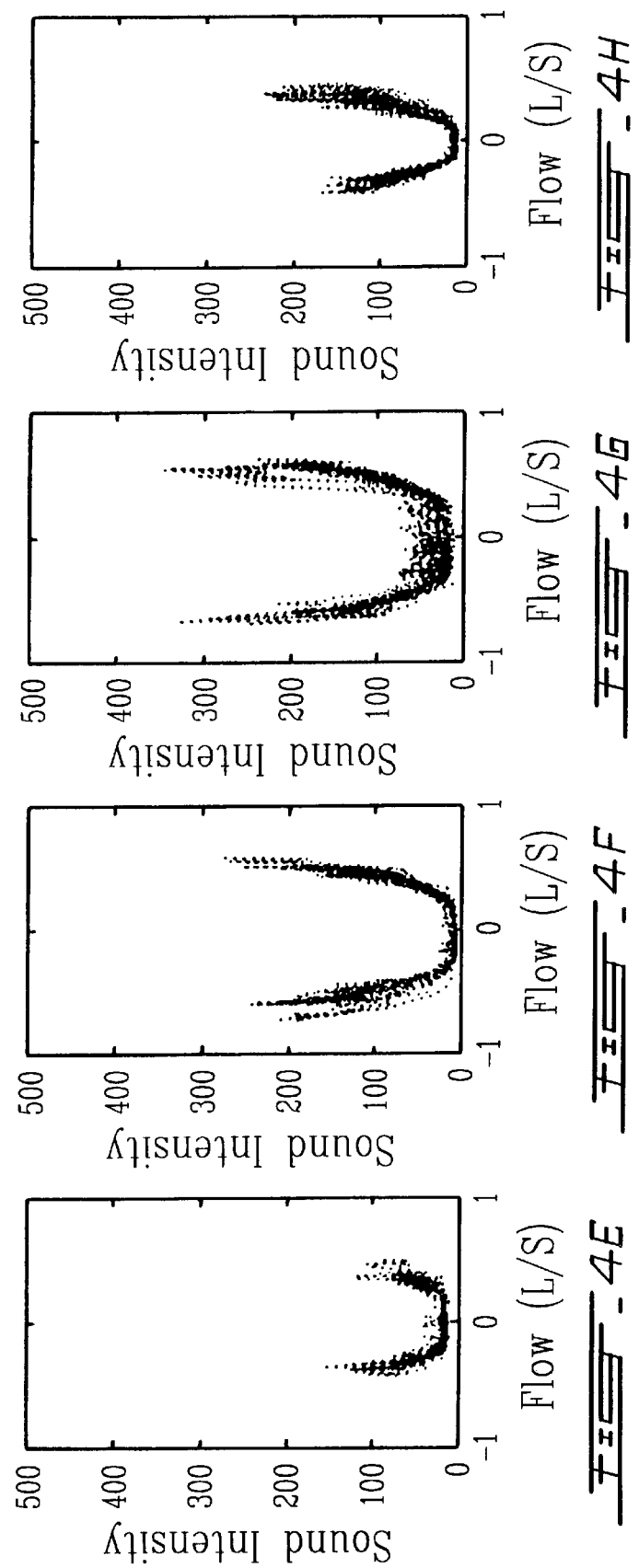

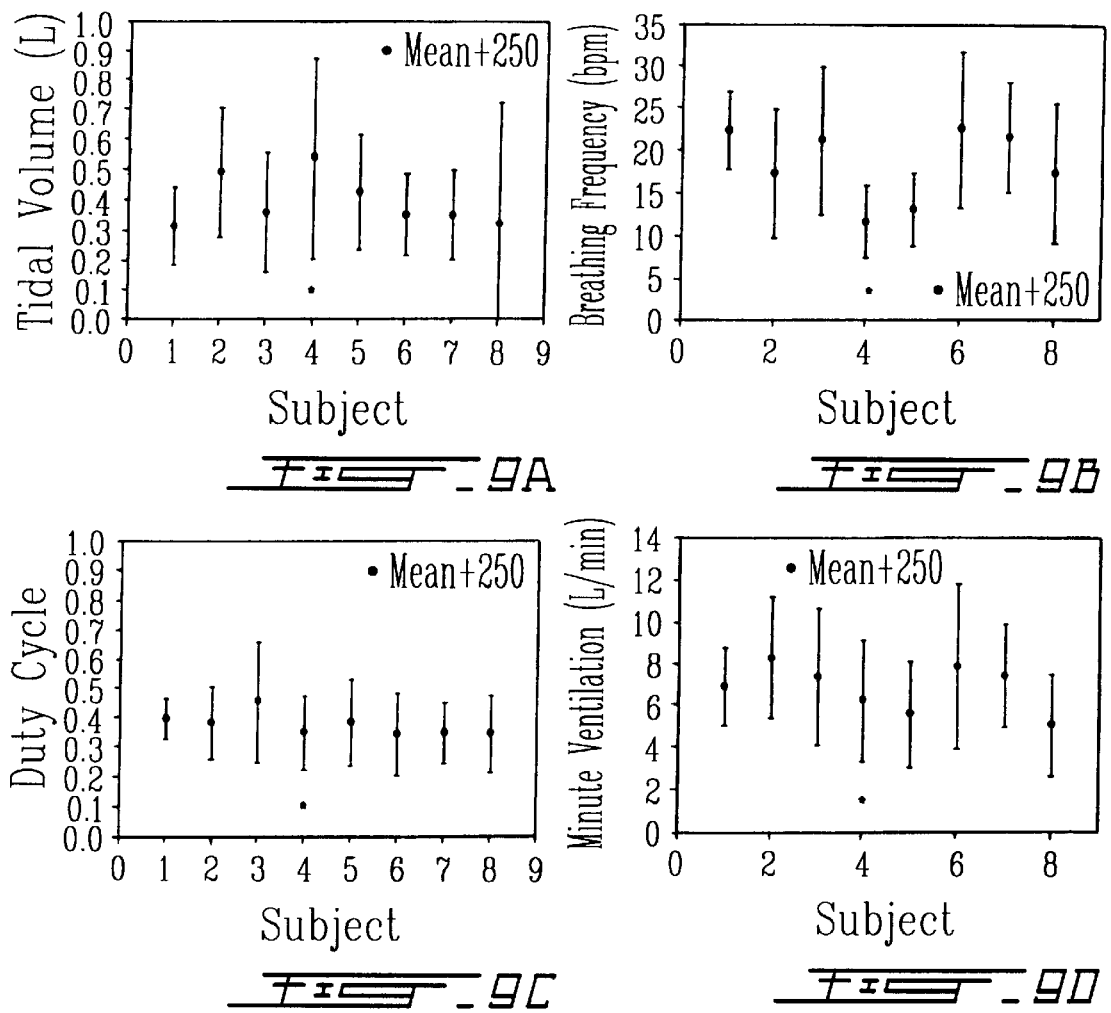

PHONOSPIROMETRY FOR NON-INVASIVE MONITORING OF RESPIRATION

FIELD OF THE INVENTION

The present invention relates to a method and apparatus of phonospirometric signal processing. More specifically, the invention relates to converting a breathing audio signal into a breath volume signal. The invention also relates to a method and apparatus for obtaining a diagnosis and/or a prognosis of a respiratory disease.

BACKGROUND OF THE INVENTION

Although there are many diseases which affect breathing and some of these are potentially fatal, a means to measure and monitor ventilation in spontaneously breathing patients for even short periods of time without rigid constraints on posture, is not known in the art. Long term ventilatory monitoring cannot be done by any known method unless a patient is intubated. This is a major problem. Patients are frequently admitted to intensive care units because the physician feels that intubation and mechanical ventilation may be required. A system that could measure and monitor ventilation would detect if the patient's ability to breathe is improving or deteriorating in time and would provide the physician with crucial information allowing him/her to make a better-informed decision. Using an alarm system, a respiratory arrest would result in almost instantaneous resuscitation because the potentially fatal event would be detected as soon as it occurs.

Babies, particularly premature ones, are at risk of the sudden infant death syndrome (SIDS) which is usually attributed to a prolonged respiratory arrest. It is known that interbreath interval is more variable in premature compared to normal term babies. Thus noninvasive measurement of ventilation could identify babies at risk for SIDS and high risk babies could be monitored by the system so that if a respiratory arrest occurred it could be identified and virtually immediately corrected.

Sleep disordered breathing is extremely common, but unfortunately no accurate means exist to measure and monitor breathing during sleep. Long term monitoring of ventilation could prove to be of great importance in diseases such as asthma and emphysema just as Holter monitoring is useful in detecting and diagnosing cardiac arrhythmias. Thus, clinical medicine has great need for a method to measure and monitor ventilation and its parameters so that respiratory arrest can be diagnosed and immediately treated; so that in patients at risk, deterioration of the ability to breathe can be detected early; so that infants at risk for SIDS can be identified and monitored; for the diagnosis of sleep-disordered breathing and for recovery of ventilatory abnormalities that had not previously been known to exist.

Precise monitoring of ventilation is presently achieved by having the subject breathe through a mouthpiece or face mask attached to a pneumotachygraph or spirometer. While these devices permit the accurate measurement of lung volumes, they also alter the pattern of breathing and the minute ventilation ($V_E$). In addition, they are useful only for occasional measurement of respiratory parameters. Long term monitoring of ventilation requires a device which would permit freedom of movement and eliminate the need for a mouthpiece and nose clip.

More versatile means of measuring ventilation are presently available. These methods (Magnetometry and Respitrace®) record the movements of the ribcage and abdomen during respiration and, by the use of suitable calibrations, convert the summed thoracic and abdominal motions into a volume signal. While these devices eliminate the need for a mouthpiece and, as a result, permit measurement of volumes and timing parameters representative of normal breathing, their calibration changes with posture, particularly changes in xiphi-pubic distance.

Monitoring and measuring respiration "non-invasively" by converting a tracheal sound signal to an airflow signal has been studied by others in the past with limited success. Phonospirometry, the estimation of ventilation from measurements of tracheal breath sounds, provides a simple alternative to Respitrace® and magnetometry, and may prove to be more versatile. Since the invention of the stethoscope by René Laennec in 1819, auscultation has provided the clinician with a quick, if crude, assessment of pulmonary ventilation. Objective measurements of breath sounds were first made more than twenty-five years ago, but it is only with advances in computer technology and the wide application of digital signal processing or numerical analysis that recording and analysis of respiratory sounds has accelerated. Lung sounds can be either normal or adventitious. Normal lung sounds appear to be primarily generated by the complex turbulence within the large and medium sized airways. The sound characteristics are influenced by airflow velocity and the local properties of the airways. As a result, for a given subject and microphone position, sound intensity is proportional to the flow rate (Leblanc, P.; Macklem, P. T.; Ross, W. R. D. Breath sounds and distribution of pulmonary ventilation. American Review of Respiratory Disease 102:10–16;1970, (Shykoff, B. E.; Ploysongsang, Y. ; Chang, H. K. Airflow and normal lung sounds. American Review of Respiratory Disease 437:872–876;1988), (Graviely, N.; Cugell, D. W. Airflow effects on amplitude and spectral content of normal breath sounds. J. Appl. Physiol. 80:5–13, 1996)

Many investigators presently measure airflow by acoustical techniques (Ajmani, A.; Mazumdar, J. ; Jarvis, D.—Spectral analysis of an acoustic respiratory signal with a view to developing an apnea monitor Australasian Physical & Engineering Sciences in Medicine 19:46–52;1996) (Makarenkov, A. P.; Rudnitskij, A. G.—Diagnosis of lung pathologies by two-channel processing of breath sounds Akusticheskii Zurnal 41:272–277;1994) (Pasterkamp H.; Kraman, S. S.; Wodicka, G. R. Respiratory sounds. Advances beyond the stethoscope. American Journal of Respiratory and Critical Care Medicine 156:974–987;1997) (Soufflet, G.; Charbonneau, G.; Polit, M.; Attal, P.; Denjean, A.; Escourrou, P.; Gaultier, C.—Interaction between tracheal sound and flow rate: a comparison of some different flow evaluations from lung sounds IEEE Transactions on Biomedical Engineering, vol. 37, No. 4, April 1990), however, their interest lies mainly in the derivation of parameters related to the frequency spectrum of the sound signal rather than in the use of the sound signal as a surrogate for flow. The papers by Shykoff et al. and Graviely and Cugell measure the relationship between sound and flow, only at flow rates greater than 0.5 lps. At flow rates less than 0.5 lps, almost no sound is detectable, and the background noise makes the signal-to-noise ratio very high. In Soufflet et al., the results reported would indicate that flows less than 0.5 lps were measured, however,. there is no indication how the problem of low flow rate can be solved.

In the known prior art, there is difficulty in recording sound intensity in the trachea and converting the sound signal into the appropriate flow signal. Typically, when the flow rate is low (e.g. less than 0.5 liters per second) conversion of the sound signal into a flow signal is not reliable enough for scientific or medical purposes. In the known prior art, there is no method for obtaining a reliable conversion of a tracheal sound signal into a flow signal in normal breathing which includes portions of low flow rates.

SUMMARY OF THE INVENTION

It is an object of the present invention to provide a method and apparatus for using acoustical data obtained from both healthy and sick humans (or other animals) to obtain a measurement of air flow during breathing. It is a further object of the present invention to provide an apparatus and method for calibrating such a phonospirometer using a pneumotach.

It is furthermore an object of the present invention to provide a method and apparatus for the diagnosis and/or prognosis of respiratory diseases. The method and apparatus for diagnosis or prognosis involves using airflow data obtained by acoustic measurements which are obtained non-invasively and without inconveniencing a patient wearing the apparatus for extended periods of time. The apparatus according to the invention could be provided in a portable or ambulatory device made using state-of-art electronic components and electronic circuits integrated in a miniature housing.

According to one aspect of the invention, there is provided a method for obtaining a volume of respiration signal from a sound signal representing respiration. The method comprises detecting a respiration start/stop and comparing the intensity of the sound signal to a threshold to determine whether the sound signal intensity is sufficiently strong with respect to the background noise so as to provide a reliable measure of tracheal flow. The sound signal is then transformed into a flow signal through integration and rectification and values are interpolated for the flow signal when the sound signal intensity is below the allowable threshold. The flow signal and the interpolated values are then integrated over either an inspiration cycle or an expiration cycle to obtain a volume of breath signal for at least one of the cycles. The volume of breath signal for an expiration cycle over a large number of cycles is equal to the volume of breath signal for an inspiration cycle.

In accordance with a second aspect of the present invention, there is provided an apparatus for non-invasive monitoring of respiration comprising at least one microphone for obtaining a sound signal from a person, represented by the person's respiration. There is also provided means for transforming the sound signal to a flow signal and means for interpolating values for the flow signal when the sound signal is below a threshold value. Integrator means are also provided to produce a volume signal of the respiration signal from the flow signal.

In so doing, we will be able to derive tidal volume by integration of the flow signal and frequency, inspiratory time, expiratory time and other ventilatory parameters from the envelope of the sound signal. The small size of the microphone and its amplifier and the location of the microphone on the neck permit the freedom of movement and function that is essential to the development of a long-tern monitoring device. In addition, since a mouth piece and nose clip are not necessary, respiratory parameters are those of normal breathing and the signals can be used to determine the variations in volume and respiratory timing which may be diagnostic of respiratory illness

BRIEF DESCRIPTION OF THE DRAWINGS

The invention will be better understood by way of the following detailed description of a preferred embodiment of the invention with reference to the appended drawings, in which:

FIG. 1B is a schematic block diagram of the measurement apparatus according to the preferred embodiment;

FIG. 1D is a schematic block diagram of a diagnosis apparatus according to the preferred embodiment; and FIGS. 2 through 10 are graphs illustrating various relationships of measured parameters involved in the present invention.

DETAILED DESCRIPTION OF THE PREFERRED EMBODIMENT

Figure 1A:
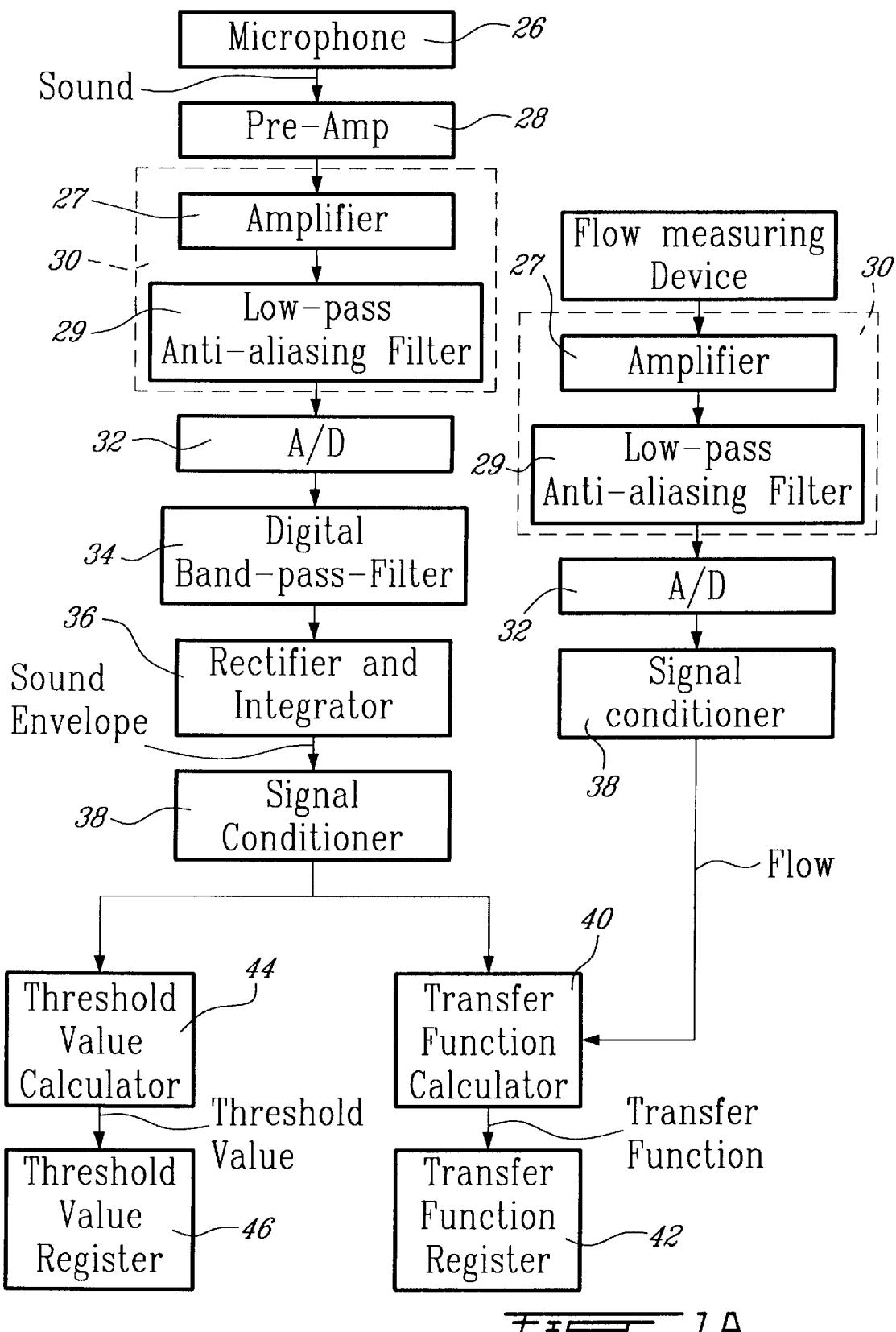
FIG. 1A is a schematic block diagram of the calibration apparatus according to the preferred embodiment.

Prior to describing the operation of the apparatus according to the preferred embodiment, brief descriptions of various components as illustrated in FIGS. 1A, 1B and 1D are provided hereinbelow.

Signal Conditioner

Subsamples and filters both the flow and sound envelope signals. Subsampling results in reduction of the number of data points. For example, subsampling by a factor of 50 reduces the sampling frequency from 3000 Hz to an effective sampling frequency of 60 Hz. The subsampling process acts as the first step of a filter as it is carried out by taking the mean of the 100 nearest neighbors of every 50th data point. The sound envelope noise is then further reduced with a second-order least-squares filter.

Threshold Value Calculator

Determines the threshold value above which flow and sound are related, either by inspection or by calculating the average of the sound envelope's mean and minimum values.

Transfer Function Calculator

Calculates the functions which relate sound to flow. Performs a regression analysis on corresponding sound envelope and flow values which exceed the threshold value. Inspiratory and expiratory flows are analyzed separately so two different transfer functions are put out.

Inspiration Start/Stop Detector

Determines whether a given sound envelope is inspiratory or expiratory by identifying the points of transition between the two states. This can be done by visual inspection of the output signal of the signal conditioner. In an automated system, the determination of inspiration start/stop can be done by an algorithm which identifies, from all the local minima of the output signal of the signal conditioner, those corresponding to the onset and the end of the inspiratory phase and those corresponding to the onset and end of the expiratory phase. This can be done by low-pass filtering the envelope signal in order to remove the frequencies above the innate breathing frequency and then picking out all the local minima in the resulting data The algorithm could also utilize timing information obtained from signals recorded by other methods for measuring the instantaneous dimension of the rib cage and/or abdomen. Such signals may be obtained using a magnetometer or Respitrace signal of either rib cage or abdominal dimensions by measuring when the rate of change of either dimension is zero at the beginning and end of a breath. Other physical method of detecting inspiration start/stop are of course possible, such as strain gauge transducers or accelerometers, etc.

Variance Calculator

Takes as input the breath-by-breath values of the ventilation parameters (Vx) where x can represent f, Ti, Te, etc. The mean value of each parameter (Vx) is calculated and then the squared difference between each value and the mean is calculated $(Vx-\overline{Vx})^2$. This value is called variance and gives an estimate of how far the parameter for a given breath deviates from the mean. Bins are chosen which span the range of variation of the parameter and the number of variance values which fit in the bin calculated. The bin value and the number of values in the bin are then plotted against one another in log-log space and the linear regression obtained. Both the slope and the intercept of this relation provide information about parameter variability and can be used diagnostically since respiratory disorders are characterized by altered variability in breathing patterns. Comparison of the variance of the parameters derived from the sound signal of patients to those obtained from normal subjects permits a decision to be made whether the individual is, for example, at risk of an adverse event such as respiratory arrest and whether the risk is sufficiently high to require a therapeutic intervention.

Methods

Subjects

Seven normal volunteers with no history of pulmonary diseases or recent respiratory tract infection, two asymptomatic mild asthmatics and four patients with unstable airways obstructions, were recruited for study. The subjects, six males and seven females, were between 30 and 75 years of age.

Procedure

Figure 1C:
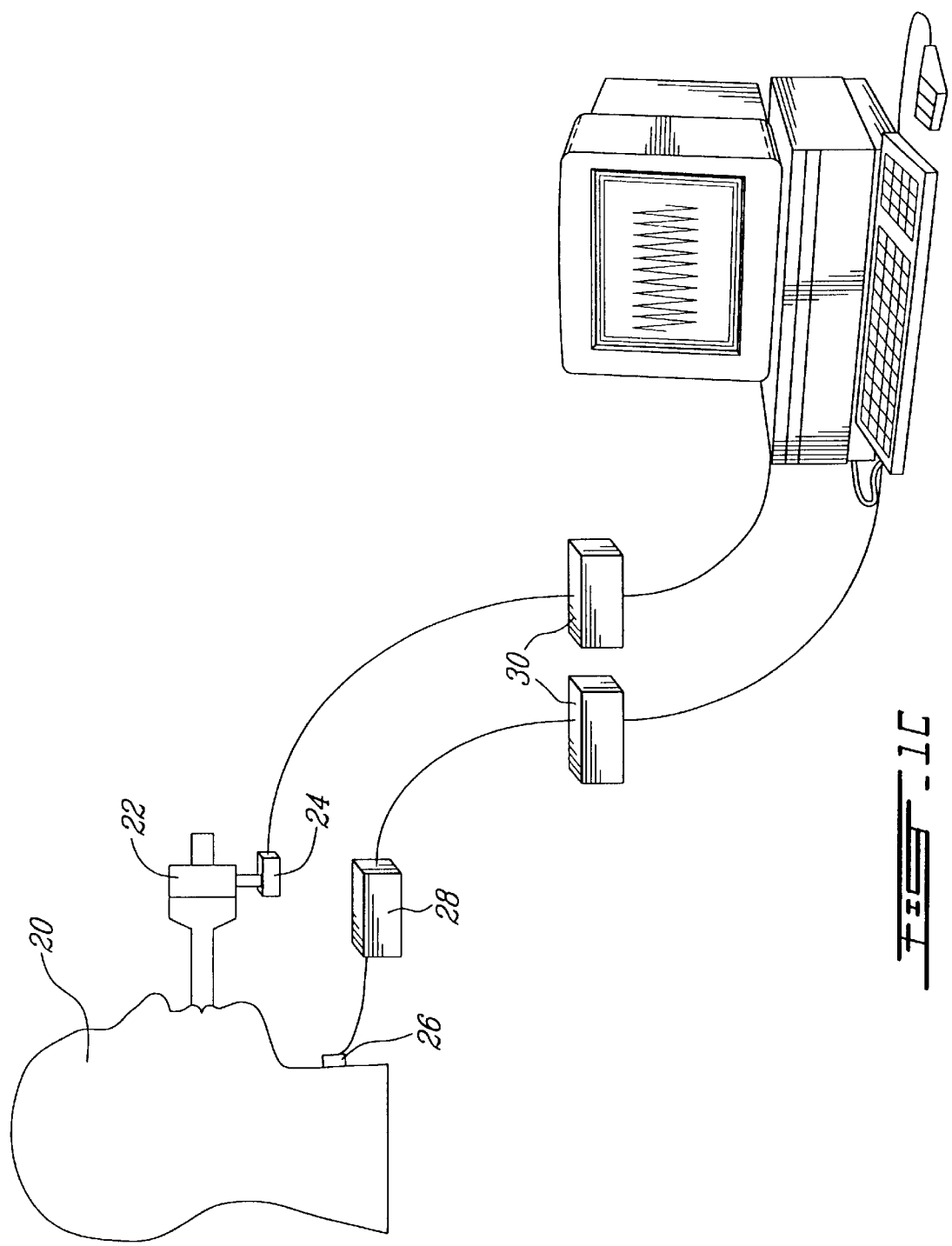
FIG. 1C is a schematic equipment diagram of the apparatus according to the invention placed on a patient.

The experimental setup is shown in FIG. 1C. The experiments were performed in two parts. First, data was collected during two separate 30 sec periods in order to calibrate the sound signal. A schematic of this process can be seen in FIG. 1A. During these periods, airflow at the mouth and tracheal breath sounds were measured simultaneously. The subjects 20 were seated, wore a nose clip, and breathed quietly on a mouth piece. A microphone 26 was placed over the trachea in a region that had been previously determined to provide the best sound signal. The flow signal was obtained using a pneumotachygraph 22 (Fleisch, #1), and piezoelectric pressure transducer 24. The sound signal was recorded using an electret microphone 26 (model 306, Armaco, Vancouver) and a custom designed preamplifier 28 with a gain of 14. Both signals were amplified 27 and filtered 29 using anti-aliasing filters (50 Hz upper cut-off for flow and 1000 Hz for sound) before A/D conversion 32. Both signals were sampled at 3000 Hz using a commercially-available software package (ORIGIN, MICROCAL™ Software, Inc. Northampton, Mass.). The sound signal was sent through a digital band-pass filter 34 and a rectifier and integrator 36 before both signals went through the signal conditioner 38. The data obtained was used to determine the relationship between flow and sound. For each calibration period, a transfer function (see below) was obtained from the transfer function calculator 40 and was used to derive flow and volume from the other calibration period. The ratio of the derived volume to the experimentally measured volume was obtained and the transfer function which gave the best estimate of volume was used for calibration of the sound signal obtained during a subsequent ten to thirty minute period of quiet breathing.

Second, with the microphone 26 in the same place, during a ten to thirty minute period of quiet breathing in the siding position, only the sound signal was sampled. The subjects were required to remain in the seated position during the period of measurement and to refrain from moving their head. As can be seen in FIG. 1B, the schematic diagram of sound measurement, the sound signal was amplified by amplifier 27, filtered by amplifier 29 and sampled by A/D 32 as during the calibration period.

Data Analysis

Still in FIG. 1B, it can be seen that the digitized sound signal was filtered by band-pass filter 34 between 200 and 1000 Hz in order to remove heart and muscle sounds which are typically less than 200 Hz and high-frequency noise which is greater than 1000 Hz (FIG. 1B).

Since respiratory flow is approximately linearly related to the integrated sound signal or breath sound amplitude, we obtained the equivalent sound envelope by applying the Discrete Hilbert Transform to our digital data using the rectifier and integrator 36 (see pp 337–375, "Digital Signal Processing", Oppenheim et al., Prentice-Hall Inc., 1975). Specifically, the digitized data was transformed to the frequency domain using a Discrete Fourier Transform (DFT). Then, all negative frequencies, and all positive frequencies less than 200 Hz and greater than 1000 Hz were set to zero using a three point roll-off function. To provide a much better attenuation in the rejection bands of the DFT-based band-pass filter (below 200 Hz and above 1000 Hz), the three first frequency coefficients above 200 Hz and below 1000 Hz were weighted by the following coefficients: 0.022, 0.23 and 0.70 (see Rabiner, L. R.; Gold, B., and MCGonegal, C. A.—An approach to the approximation problem for nonrecursive digital filters, IEEE Trans. Audio Electroacoustics, 18(2):83–106, 1970). Following an inverse DFT, the absolute value of the signal was taken as the sound envelope.

In order to further reduce the noise, the resulting envelope signal was filtered in two steps using the signal conditioner 38. First the data was subsampled by averaging the 100 closest neighbors at every 50th data point. Subsequently, a 20-point second-order least-squares smoothing filter was applied. The flow signal was also subsampled to maintain the same frequency as the sound signal.

The relationship between flow and sound as determined from the calibration data is illustrated in FIG. 2. It can be seen from this example that the relationship is different for inspiration and expiration and, below a flow of approximately 0.3 L/s, the sound signal is not significantly different from the baseline. As a result, inspiration and expiration were analyzed separately. For each subject, a single threshold sound value above which the relation between flow and sound was approximately linear was determined and is illustrated by the threshold value of 50 (line 58) in FIG. 2. Above this threshold, the relationship (transfer function) between sound and flow was obtained by least-squares linear regression. As can be appreciated, a linear approximation is only a first order approximation, and it will be readily apparent to those skilled in the art that non-linear approximations are possible.

To analyse the 10 min. segment of data obtained during quiet breathing, the sound signal was filtered as described above and the sound envelope (intensity) obtained. The intensity signal was then visually inspected in order to determine which sections corresponded to inspiration and expiration and the appropriate transfer function was applied to points whose values exceeded the predetermined threshold. For the remaining points, since the sound signal was too weak to calculate a flow value, a linear interpolation was made to neighboring points corresponding to the beginning of inspiration or expiration, whichever was appropriate. These points were determined by visual inspection of the sound envelope and their corresponding flow value was set to zero. These points would be computed automatically by the inspiration start/stop detector in the case of a portable instrument or automated apparatus. As can be appreciated, a linear approximation for the interpolated values of flow is only a first order approximation, and it will be readily apparent to those skilled in the art that non-linear approximations are possible. It is also clear that during expiration, the flow decay is not normally linear.

Effect of Position

Because head movements and changes of posture are to be expected in long-term monitoring, we examined the correspondence between measured and estimated flow signals during systematic change in head and body position. In three subjects, flow and sound signals were measured during up-and-down and right-to-left movements of the head.

Results

Filtering of sound signal

Flow and the corresponding sound signal obtained during a calibration run are illustrated in FIGS. 3A and 3B, respectively. During a single breath, two sound bursts were observed, one during inspiration, the other during expiration. Sounds in phase with the heart beat can be seen as sharp spikes. After band-pass filtering (FIG. 3C), there was a marker attenuation of the background noise and the cardiac artifact and good preservation of the sound signal. Rectification and integration of this signal by Discrete Hilbert transform gave the sound envelope (FIG. 3D) which is an index of the sound intensity.

The relationship between sound intensity and flow for all breaths of a single calibration period is plotted in FIG. 2. Below approximately 0.3 L/min, the sound intensity did not exceed the background noise either because the microphone was not sensitive enough or the tracheal flows were not high enough to generate sound. A threshold sound value above which there was a clear relation between sound and flow was thus defined and is illustrated as the solid line in the figure. The transfer function was calculated using only sound values above this threshold and their corresponding flow values.

The relationship between sound intensity and flow in all subjects is illustrated in FIG. 4. The general shape is similar for all subjects although there were variations in sound intensity at a given flow from subject to subject as well as in the flow value above which tracheal sounds could be detected.

Figure 5A:
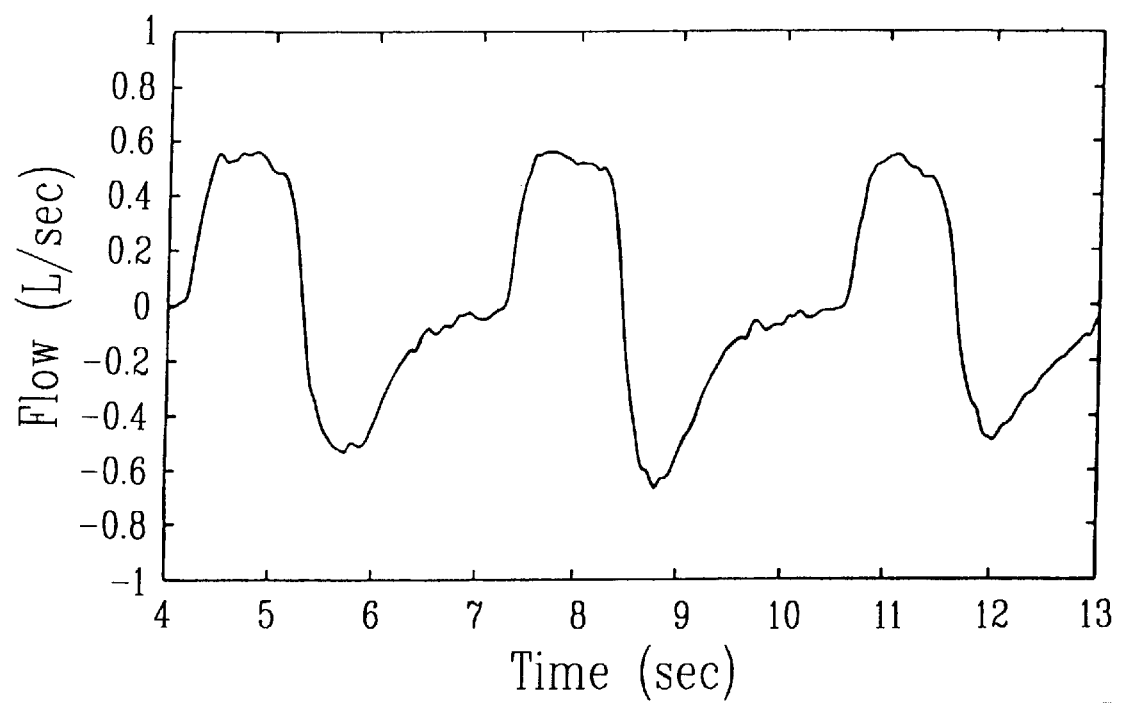
Figure 5B:
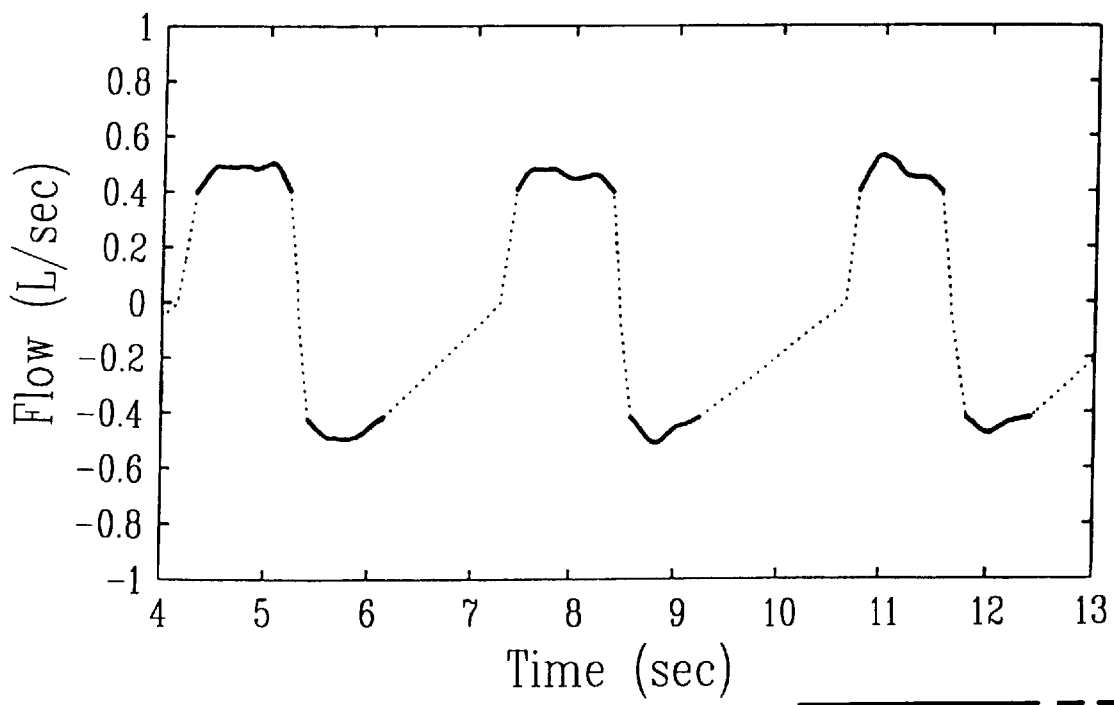
Figures 6A, 6B, 6C, 6D, 6E, 6F, 6G, 6H:
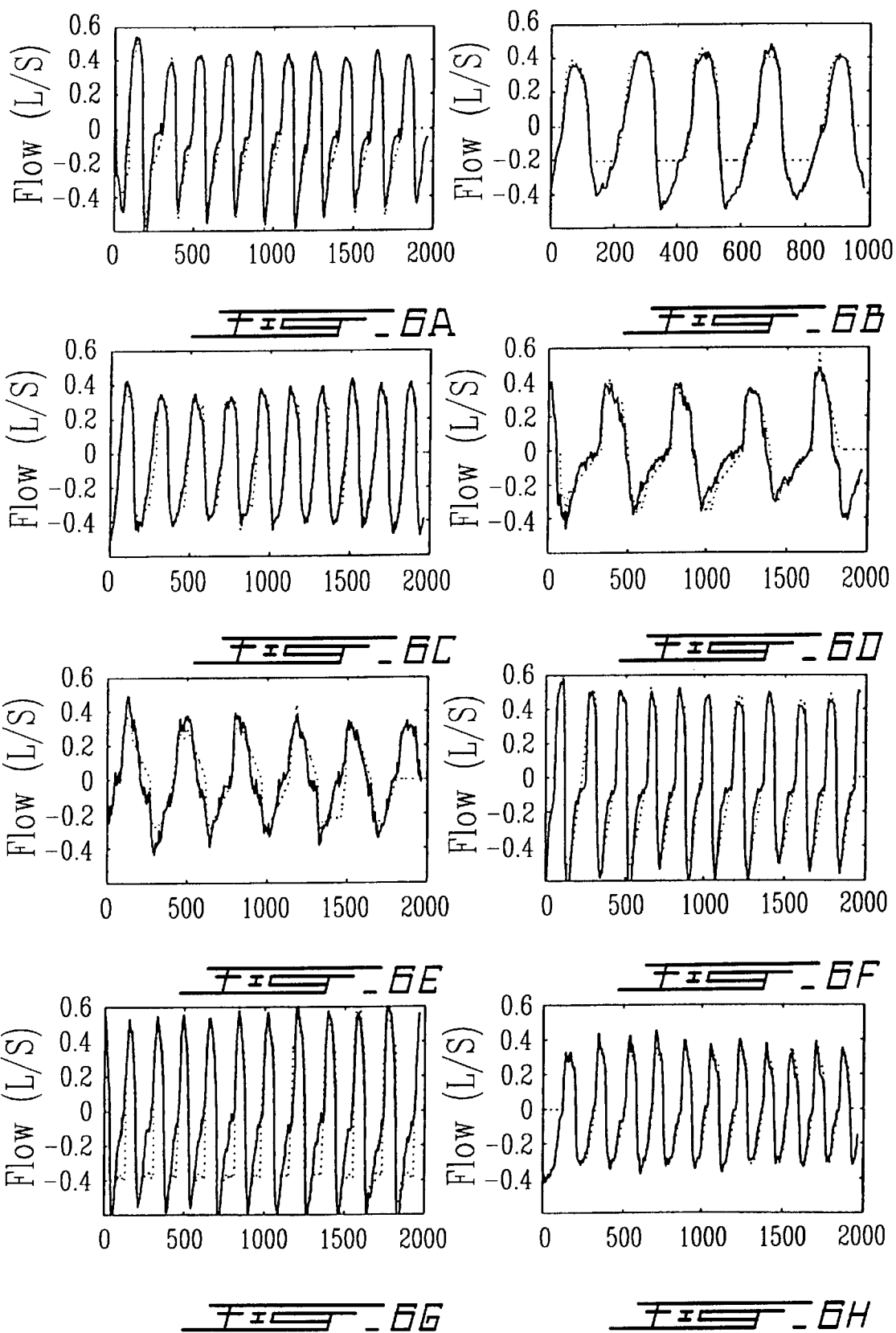

In FIG. 5, the flow signal derived from the sound signal (lower panel) is compared to the measured flow signal (upper panel). The solid dark line segments in the lower panel represent the calculated flows and the dotted lines, the interpolated values. It can be seen from this illustration that the interpolated values are close to the actual flows during inspiration and the beginning of expiration but that the correspondence was not good during the latter part of expiration because of the concave shape of the actual flow curve. The error was greatest when the subjects had a long end-expiratory pause. FIG. 6 shows measured (solid lines) and calculated (dotted lines) flows for all 8 subjects. In subjects CL, QZ, SK, QLZ, and SW, the two flow signals were very close while in the remaining 3 subjects there were significant differences between the two. These differences were greatest during expiration and in all subjects the two signals were very similar during inspiration. As a result, tidal volume was calculated using the inspiratory flow signal.

Validation of transfer functions

Since we are more interested in volume than flow, we used the error in volume estimation as our index of accuracy for the technique. The estimated flow was calculated using the sound signal of one calibration file and the transfer function derived from the other calibration run in the same subject. Volumes were obtained from integration of the flow signals. For each breath, the error was calculated as the absolute value of the percent difference between estimated (Ve) and measured (Vm) volumes $$\left|\left(\frac{Ve-Vm}{Vm}\right)\times 100\right|.$$

The average error, determined for each of the 8 subjects, was between 5.82 and 12.70% (mean 8.86% give SD).

Figures 7A, 7B, 7C, 7D:
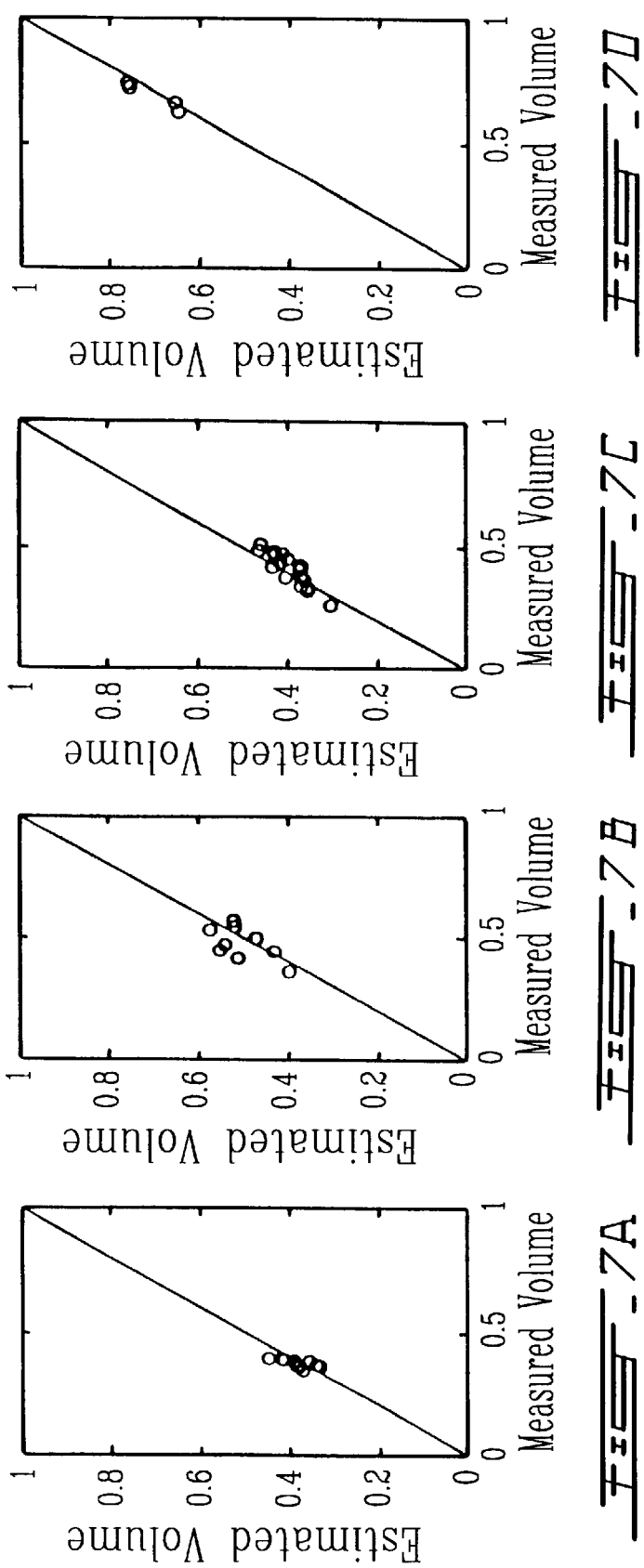
Figures 7E, 7F, 7G, 7H:
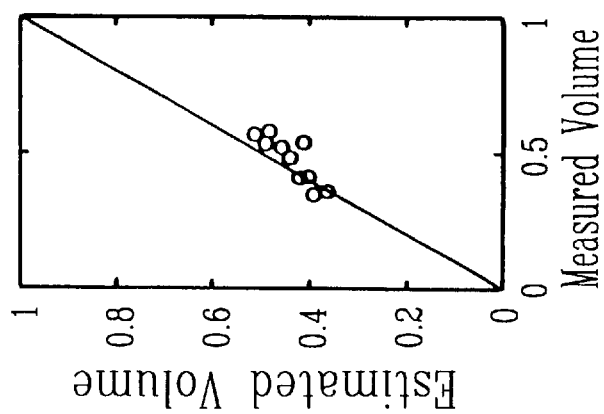

A comparison of Ve and Vm for each of the 8 subjects is given in FIG. 7. The solid lines represent the line of identity.

In all subjects, the data points fall close to the identity line indicating the close correspondence between Ve and Vm. However, in some subjects there were systematic differences between Ve and Vm suggesting that the method will consistently over- (as in EB or QL) or underestimate (as in SW) the tidal volume.

Variation of Natural Breathing

Figure 8:
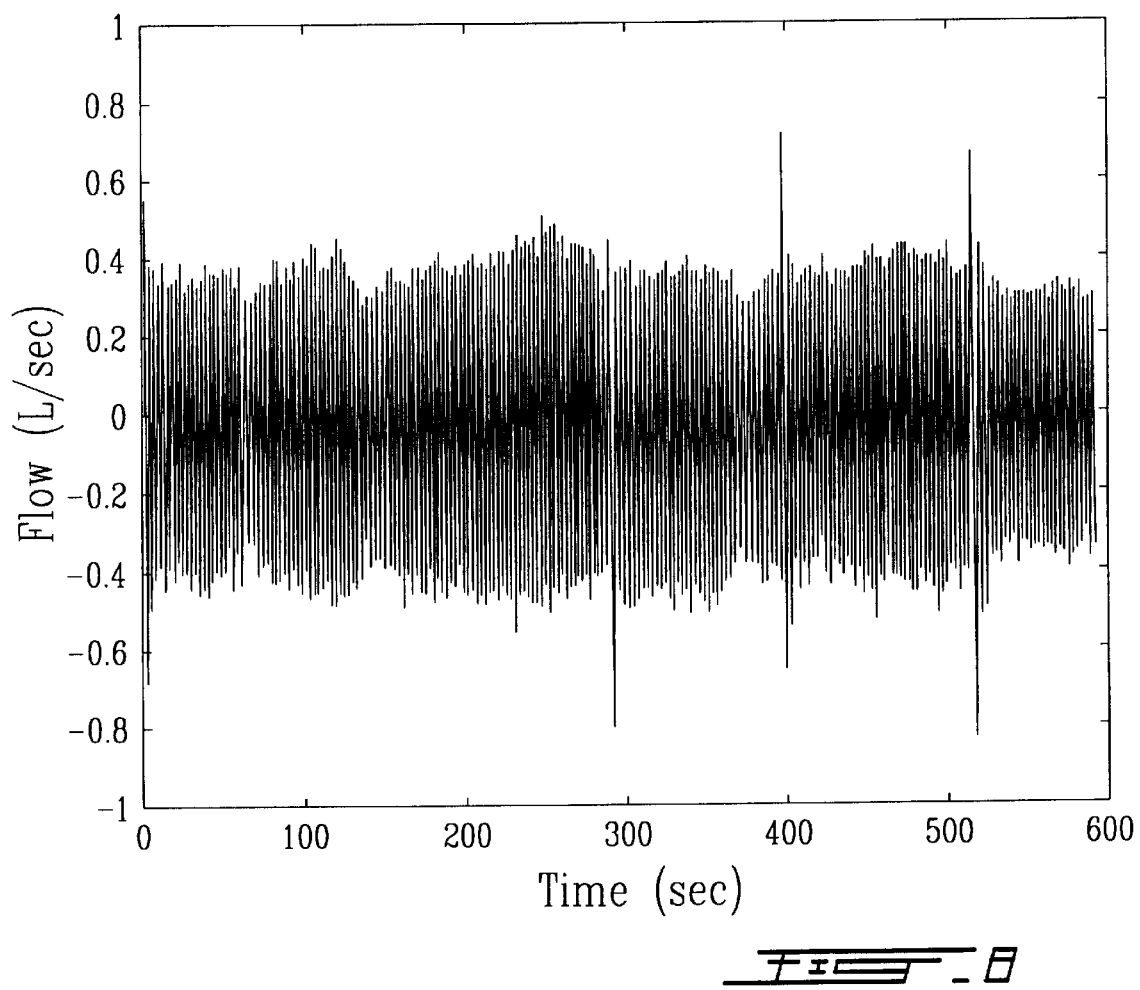

From the ten-minute sound signal, we calculated breath-by-breath values of $V_T$, $V_E$, Ti, Ttot, breathing frequency, and duty cycle for each subject during the ten minute period of quiet breathing. The variation in natural breathing in a single subject is illustrated by the flow signal in FIG. 8. Inspiratory and expiratory flows appeared to vary cyclically during the ten minute breathing period. In addition, there were occasional large flow transients which likely represented sighs. Variability in tidal volume for the eight subjects is shown in FIG. 9, upper left panel. Tidal volume (upper right panel) differed markedly both among the subjects and within subjects as did breathing frequency (upper right panel). $V_T$ ranged from 0.31±0.06 to 0.54±0.17 L and breathing frequency from 11.69±2.09 to 22.23±2.26 bpm. Minute ventilation (FIG. 9, lower right) was less variable, ranging from 5.03±1.22 to 8.27±1.47 L/min, perhaps because those subjects with the largest tidal volumes had the lowest frequencies. The patients with unstable airway obstructions had increased minute ventilation due mainly to an increase in mean inspiratory flow. Ti (inspiratory time) ranged from 0.92±0.15 to 1.80±0.34 sec, while duty cycle only varied from 0.34±0.07 to 0.45±0.10. Examination of the coefficients of variation (CV) indicated that duty cycle was the least variable parameter, (range, 0.08 to 0.20), while $V_T$ was the most variable, (range, 0.19 to 0.62); breathing frequency (range, 0.10 to 0.23) and $V_E$ (range, 0.14 to 0.24) having moderate CV's.

Effect of head movements volume estimation was markedly affected by the change in head position, but, overall, the effect was small. These data suggest that the transmission of sound is not markedly altered by changes in position of the head so that the transfer function derived in one position is applicable to a range of head positions.

What is claimed is:

1. A method for obtaining a volume of respiration signal from a sound signal representing respiration, the method comprising:
    detecting respiration start/stop;
    comparing an intensity of said sound signal to a threshold to determine whether said sound signal intensity is sufficiently strong with respect to background noise so as to provide a reliable measure of tracheal flow;
    transforming said sound signal to a flow signal;
    interpolating values for said flow signal when said sound signal intensity is below said threshold; and
    integrating said flow signal and said interpolated values of said flow signal over at least one of an inspiration cycle and an expiration cycle to obtain a volume of breath signal for said at least one cycle.

2. The method as claimed in claim 1, wherein said at least one cycle is inspiration, and said interpolating comprises:
    firstly interpolating said flow signal during inspiration from a point of detecting said respiration start/stop at which said flow is determined to be zero until said sound signal intensity reaches said threshold and has a value determined by said transforming; and
    secondly interpolating said flow signal at an end of said inspiration cycle as said sound signal intensity drops below said threshold at an end of inspiration and a zero flow value point determined using a function continuous between said flow signal value at a point where said sound signal intensity drops below said threshold and said flow signal value at a point where said sound signal intensity rises above said threshold at a beginning of expiration.

TABLE 1

Effect of head position on Ve/Vm

| Subject | Forward | | Up | | Down | | Forward | | Left | Right |
|---------|---------|---|-----|---|------|---|---------|---|------|-------|
| C.-L.   | 1.03 0.07 | ± | 1.0 0.22 | ± | 0.99 0.21 | ± | 1.09 0.14 | ± | 0.91 ± 0.14 | 0.86 ± 0.03 |
| S.Y.    | 0.92 0.08 | ± | 1.03 0.18 | ± | 1.06 0.16 | ± | 1.13 0.08 | ± | 1.20 ± 0.27 | 0.99 ± 0.22 |
| J.H.    | 1.00 0.21 | ± | 1.40 0.43 | ± | 1.09 0.28 | ± | 1.03 0.07 | ± | 0.85 ± 0.26 | 1.11 ± 0.08 |

Figure 10A:
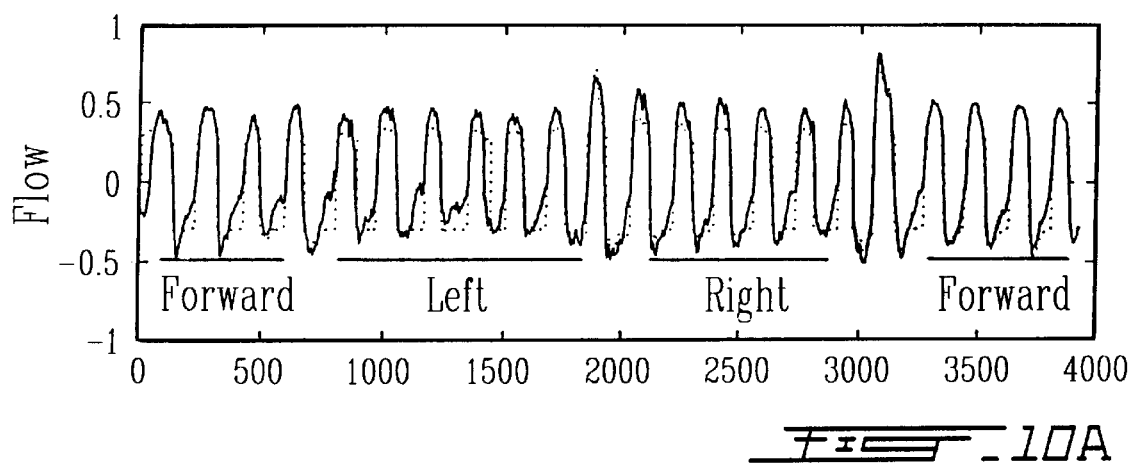
Figure 10B:
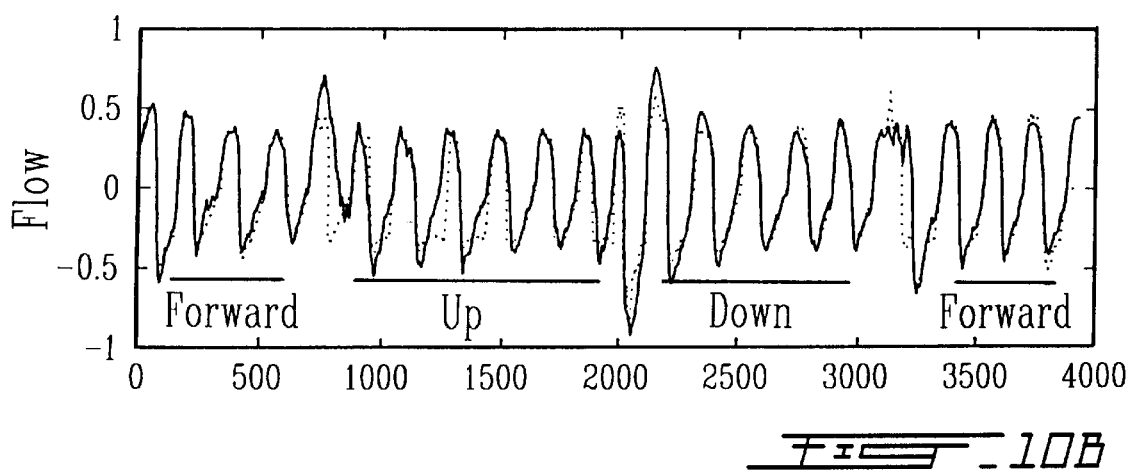

In FIG. 10, the flow signal derived from tracheal breath sounds (dotted line) is compared to the directly measured flow (solid line) during head movements in a single subject. The upper panel shows data obtained when the head was moved from side-to-side. The lower panel illustrates up-and-down movements of the head. In this subject, the correspondence between the measured and the estimated flow signal was good no matter what the position of the head. The breaths during the transition from one position to another tended to be larger than the preceding and following breaths and could be readily identified. They also were less well described by the estimated flow signal. The ratio of estimated volume to measured volume (Ve/Vm) for each subject in all positions is given in Table 1. In some instances the 3. The method as claimed in claim 1, wherein said volume of breath signal is obtained only for said inspiration cycle, said volume of breath signal for said expiration cycle over a large number of cycles being equal to said volume of breath signal for said inspiration cycle.

4. The method as claimed in claim 3, wherein said steps of comparing and transforming involve analysis which is the same for both inspiration and expiration.

5. The method as claimed in claim 2, wherein said firstly and said secondly interpolating comprises linear interpolating.

6. The method as claimed in claim 1, further comprising a step of averaging said volume signal over time to obtain a tidal volume signal.

7. The method as claimed in claim 3, further comprising a step of averaging said volume signal over time to obtain a tidal volume signal.

8. The method as claimed in claim 1, wherein said step of detecting respiration start/stop comprises analyzing said sound signal.

9. The method as claimed in claim 1, wherein said step of detecting respiration star/stop comprises physically measuring at least one of chest and abdomen position or motion.

10. The method as claimed in claim 1, further comprising a step of monitoring a time of said respiration start/stop to obtain a respiratory frequency signal.

11. The method as claimed in claim 1, further comprising a step of averaging said flow signal during inspiration and generating a mean inspiratory flow signal.

12. The method as claimed in claim 1, further comprising a step of calibrating a sound signal to flow signal transform function by measuring treacheal flow directly while recording said sound signal over a period of time and setting parameters of said transform function to provide flow values corresponding to said measured tracheal flow.

13. The method as claimed in claim 3, further comprising a step of calibrating a sound signal to flow signal transform function by measuring tracheal flow directly while recording said sound signal over a period of time and setting parameters of said transform function to provide flow values corresponding to said measured tracheal flow.

14. An apparatus for non-invasive monitoring of respiration comprising:

at least one microphone for obtaining a sound signal from a person, said sound signal representing respiration;

means for detecting inspiration start and stop;

means for transforming said sound signal to a flow signal, said transforming means receiving data from transfer function register means and threshold value register means;

means for generating interpolated values for said flow, signal when said sound signal is below said threshold value; and integrator means for integrating said flow signal to produce a volume of respiration signal.

15. The apparatus as claimed in claim 14, further comprising an alarm circuit for processing said volume of respiration signal and generating an alarm signal when said volume of respiration signal has characteristics representing a condition in need of medical attention.

16. A method for obtaining at least one of a diagnosis and a prognosis of a respiratory disease comprising the steps of:

placing at least one microphone on a patient to obtain a sound signal from respiration of said patient;

processing said sound signal to obtain a volume of respiration signal;

monitoring said volume of respiration signal over time;

analyzing said volume signal over time to obtain at least one parameter indicative of said diagnosis and/or prognosis.

17. The method as claimed in claim 16, wherein said step of processing comprises:

detecting respiration start/stop;

comparing an intensity of said sound signal to a threshold to determine whether said sound signal intensity is sufficiently strong with respect to background noise so as to provide a reliable measure of tracheal flow;

transforming said sound signal to a flow signal;

interpolating values for said flow signal when said sound signal intensity is below said threshold; and integrating said flow signal and said interpolated values of said flow signal over at least one of an inspiration cycle and an expiration cycle to obtain a volume of breath signal for said at lest one cycle.

18. The method as claimed in claim 17, wherein said at least one cycle is inspiration, and said interpolating comprises:

firstly interpolating said flow signal during inspiration from a point of detecting said respiration start/stop at which said flow is determined to be zero until said sound signal intensity reaches said threshold and has a value determined by said transforming; and secondly interpolating said flow signal at an end of said inspiration cycle as said sound signal intensity drops below said threshold at an end of inspiration and a zero flow value point defined using a function continuous between said flow signal value at a point where said sound signal intensity drops below said threshold and said flow signal value at a point where said sound signal intensity rises above said threshold at a beginning of expiration.

19. The method as claimed in claim 18, wherein said volume of breath signal is obtained only for said inspiration cycle, said volume of breath signal for said expiration cycle over a large number of cycles being to said volume of breath signal for said inspiration cycle.

20. The method as claimed in claim 17, further comprising steps of:

attaching a wearable eye device to said patient, said device having signal processing means for carrying out said step of processing; and analyzing said volume of breath signal and generating an alarm when said volume of respiration signal has characteristics representing a condition in need of medical attention.

* * * * *